United States Patent [19]

Robertson et al.

[11] Patent Number: 5,356,934

[45] Date of Patent: * Oct. 18, 1994

[54] SELECTED SEROTONIN SUBTYPE RECEPTOR AGONIST TO TREAT SLEEP APNEA

[75] Inventors: David W. Robertson, Greenwood; David T. Wong, Indianapolis, both of Ind.

[73] Assignee: Eli Lilly and Company, Indianapolis, Ind.

[ * ] Notice: The portion of the term of this patent subsequent to Oct. 5, 2010 has been disclaimed.

[21] Appl. No.: 80,597

[22] Filed: Jun. 21, 1993

Related U.S. Application Data

[63] Continuation of Ser. No. 946,827, Sep. 16, 1992, abandoned, which is a continuation of Ser. No. 501,060, Mar. 29, 1990, abandoned.

[51] Int. Cl.$^5$ ............................................. A61K 31/135
[52] U.S. Cl. ..................................................... 514/649
[58] Field of Search ........................................ 514/649

[56] References Cited

U.S. PATENT DOCUMENTS

| | | | |
|---|---|---|---|
| 4,018,895 | 4/1977 | Molloy et al. | 514/649 |
| 4,035,511 | 7/1977 | Messing et al. | 514/651 |
| 4,194,009 | 3/1980 | Molloy et al. | 514/651 |
| 4,314,081 | 2/1982 | Molloy et al. | 564/347 |
| 4,594,358 | 6/1986 | Hynes | 514/651 |
| 4,698,342 | 10/1987 | Crosby | 514/253 |
| 4,738,973 | 4/1988 | Gittos | 514/328 |
| 4,843,071 | 6/1989 | Hohenwarter | 514/217 |
| 4,918,207 | 4/1990 | Brown et al. | 549/504 |
| 5,250,571 | 10/1993 | Fuller et al. | 514/651 |

OTHER PUBLICATIONS

Syvalahti et al., *Current Therapeutic Research* 25(2), 299 (1979).
Wong, et al., *Biochemical Pharmacology*, 32(7), 1287 (1983).
Hall, et al., *Acta Pharmacol et toxicol.*, 54, 379 (1984).
Thomas et al., *Psychopharmacology*, 93, 193 (1987).
Neill et al., *Psychopharmacology*, 99(2), 196–201 (1989).
Fuller et al., Ser. No. 07/486,478 filed on Feb. 28, 1990.
Robertson et al., *J. Med Chem.*, 31 1412 (1988).
Wong et al., *Drug Development Research*, 6, 397 (1985).
Fuller et al., *Pharmacology Biochemistry and Behavior*, 24 281 (1986).
Nash et al., *Clin. Chem.*, 28(10), 2100 (1982).
Aronoff et al., *Clin. Pharmacol. Ther.*, 36(1), 138 (1984).
Williams, et al., *Sleep Disorders: Diagnosis and Treatment*, John Wiley and Sons, (1988) Chapter 4.
*Hospital Pharmacy*, 24, 62–64 (1989).
Edwards, et al., *Neuropsychopharmacology*, 3(2), 129–136 (1990).
Mueller, et al., *Acta Pharmacol. et toxicol.*, 47, 285–293 (1980).
Garner, et al., *Am. Rev. Respir. Dis.*, 139, 946–950 (1989).
Mendelson, et al., *Am. Rev. Respir. Dis.*, 141, 1527–1530 (1990).
Yoshioka, et al., *J. Pharmacol. Exp. Ther.*, 260(2), 917–924 (1992).

*Primary Examiner*—Gary E. Hollinden
*Attorney, Agent, or Firm*—Joseph A. Jones

[57] ABSTRACT

The present invention provides a method of employing (R)-fluoxetine to treat sleep Apnea.

4 Claims, No Drawings

SELECTED SEROTONIN SUBTYPE RECEPTOR AGONIST TO TREAT SLEEP APNEA

This application is continuation of application Ser. No. 07/946,827 filled Sep. 16, 1992 now abandoned which is a continuation of application Ser. No. 07/501,060 filled Mar. 29, 1990 now abandoned.

BACKGROUND OF THE INVENTION

During the past decade, the relationship between monoamine uptake and a variety of diseases and conditions has been appreciated and investigated. For example, the hydrochloride salt of fluoxetine (dl- N-methyl-3-[4-(trifluoromethyl)phenoxy]-3-phenylpropylamine) is a selective serotonin (5-hydroxytryptamine, 5HT) uptake inhibitor. Fluoxetine hydrochloride is marketed under the trademark PROZAC® for the treatment of depression. This compound is among many taught in U.S. Pat. No. 4,018,895, 4,194,009, and 4,314,081 as being potent, selective blockers of serotonin uptake.

Fluoxetine is a racemate of the two enantiomeric forms. The biological and pharmacological activity of each enantiomer has been reported to be essentially the same; see, Robertson et al., *J. Med. Chem.*, 31, 1412 (1988) and references cited therein.

we have now discovered that the (R)-enantiomer of fluoxetine is a selective agonist of $5HT_{1C}$ receptors.

SUMMARY OF THE INVENTION

This invention provides a method for selectively occupying the $5HT_{1C}$ receptor in mammals which comprises administering to a mammal requiring such agonism an effective amount of (R)-fluoxetine or a pharmaceutically acceptable salt or solvate thereof.

DETAILED DESCRIPTION AND PREFERRED EMBODIMENT

This invention includes the use of pharmaceutically acceptable acid addition salts of (R)-fluoxetine. Since (R)-fluoxetine is an amine, it is basic in nature and accordingly reacts with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate,-sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. Preferred pharmaceutically acceptable acid addition salts include those formed with mineral acids such as hydrochloric acid and hydrobromic acid, and those formed with organic acids such as fumaric acid and maleic acid.

The pharmaceutically acceptable acid addition salts of (R)-fluoxetine can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

(R)-Fluoxetine can be prepared by any of a number of methods generally known in the art. For example, there are several methods provided in the literature for making the racemate of fluoxetine, which, in turn can be resolved into its (S) and (R) components by standard methods.

Thus, (R)-fluoxetine can be prepared as reported by Robertson, et al., *J. Med. Chem,* 31, 1412 (1988), which reference is expressly incorporated into this specification by reference.

Alternatively, (R)-fluoxetine can be synthesized by the same methods as reported for preparing racemic fluoxetine employing chiral starting materials. (R)-Fluoxetine is useful as an agonist of $5HT_{1C}$ receptors. Therefore, the present invention provides a method for occupying $5HT_{1C}$ receptors in mammals which comprises administering to a mammal requiring such agonism a pharmaceutically effective amount of (R)-fluoxetine or a pharmaceutically acceptable salt thereof. The term "pharmaceutically effective amount", as used herein, represents an amount of (R)-fluoxetine which is capable of occupying $5HT_{1C}$ receptors. The particular dose of compound administered according to this invention will, of course, be determined by the particular circumstances surrounding the case, including the route of administration, the particular condition being treated, and similar considerations. (R)-Fluoxetine can be administered by a variety of routes including the oral, rectal, transdermal, subcutaneous, intravenous, intramuscular or intranasal routes. A typical daily dose will contain from about 0.01 mg/kg to about 20 mg/kg of (R)-fluoxetine. Preferred daily doses will be about 0.05 to about 10 mg/kg, ideally about 0.1 to about 5 mg/kg.

(R)-Fluoxetine has the ability to treat a variety of disorders in mammals associated with dysfunction in serotonergic systems involving the 1C receptor such as obesity, bulimia, alcoholism, pain, sleep apnea, obsessive-compulsive disorders, substance abuse (e.g., cocaine, heroin, amphetamines, etc.), and migraine.

The following experiment was conducted to demonstrate the ability of (R)-fluoxetine to affect radioligand binding to five subtypes of serotonin receptors. This general procedure is set forth by Wong et al., *Life Sciences,* 46, 231 ( 1990 ) .

Bovine choroid plexus and brain tissues from male Sprague-Dawley rats was homogenized in 9 volumes of 0.32 M sucrose. After centrifugation at 1000 ×g for 10 minutes and then at 17,000 ×g for 20 minutes, a crude synaptosomal fraction was sedimented. The pellet was suspended in 100 volumes of 50 mM Tris-HCl, pH 7.4, incubated at 37° C. for 10 minutes, and centrifuged at 50,000 ×g for 10 minutes. The process was repeated, and the final pellet of membrane was suspended in ice-chilled 50 mM Tris-HCl buffer, pH 7.4.

Binding of $^3$H-mesulergine to the $5HT_{1C}$ receptor and other serotonergic $^3$H-ligands to subtypes of 5HT receptors ($^3$H-8-hydroxy-2-(di-n-propylamino )tetralin to $5HT_{1A}$; $^3$H-serotonin to $5HT_{1B}$ and $5HT_{1D}$; $^3$H-ketanserin to $5HT_2$; and $^3$H-1-methyl-N-(8-methyl-8-azabicyclo[3.2.1]oct-3-yl) -1H-indazaole-3-carboxamide to 5HT$_3$ receptors) was performed according to the method described in the above reference. Briefly, membranes isolated from bovine choroid plexus (for 5HT$_{1C}$) or rat brain were incubated at 25° C. for 30 minutes in 2 ml of 50 mM Tris-HCl, pH 7.4; 10 mM pargyline, 0.6 mM ascorbic acid; 5 mM CaCl$_2$; and 2 nM $^3$H-mesulergine or other tritiated ligand. Binding was terminated by filtering samples under reduced pressure through glass fiber (GFB) filters. The filters were washed 3 times with 5 ml of ice cold buffer and placed in scintillation vials with 10 ml of PCS (Amersham/Searle) scintillation fluid. Radioactivity was measured with a liquid scintillation spectrometer. Serotonin at 10 μM also included in separate samples to determine specific binding, which accounted for 90-70 percent of total binding.

The results of the evaluation of (R)-fluoxetine from these experiments are set forth below in Table I. In the Table, columns 2-6 provide the micromolar (μM) concentration of the test compound needed to inhibit radioligand binding by 50% for each of the indicated receptors.

TABLE I

AFFINITIES OF (R)-FLUOXETINE FOR SUBTYPES OF SEROTONIN RECEPTORS

| Compound | Inhibition of Radioligand Binding to 5HT Receptor* | | | | | |
|---|---|---|---|---|---|---|
| | 1A | 1B | 1C** | 1D | 2 | 3 |
| (R)-fluoxetine | 23 | 22 | 0.19 | 71 | 3.1 | 16 |

*IC50 IN μM (MICROMOLAR OR 10$^{-6}$M)
**Mean of three experiments

The compound and salts employed in the present invention are preferably formulated prior to administration. These pharmaceutical formulations are prepared by known procedures using well known and readily available ingredients. The active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide quick, sustained or delayed release of the active ingredient after administration to the patient by employing procedures well known in the art.

The compositions are preferably formulated in a unit dosage form, each dosage containing from about 5 to about 100 mg, more usually about 20 to about 80 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

We claim:

1. A method for treating sleep apnea in mammals which comprises administering to a mammal requiring sleep apnea treatment an effective amount of (R)-fluoxetine or a pharmaceutically acceptable acid addition salt or solvate thereof.

2. A method of claim 1 wherein the (R)-fluoxetine is administered in the substantial absence of (S)-fluoxetine.

3. A method of claim 1 wherein the amount of (R)-fluoxetine or salt or solvate thereof is effective to alter neurotransmission of serotonin at the serotonin 1C receptor.

4. A method of claim 3 wherein the amount of (R)-fluoxetine or salt or solvate thereof is substantially ineffective to alter neurotransmission at serotonin receptors other than the 1C receptor.

* * * * *